United States Patent
Hatano et al.

(10) Patent No.: US 11,396,567 B2
(45) Date of Patent: Jul. 26, 2022

(54) FINE FLUORESCENT PARTICLE CONTAINING AIE-ACTIVE COMPOUND

(71) Applicant: National University Corporation SAITAMA UNIVERSITY, Saitama (JP)

(72) Inventors: Ken Hatano, Saitama (JP); Takahiko Matsushita, Saitama (JP); Daisuke Fujikawa, Saitama (JP); Koji Matsuoka, Saitama (JP)

(73) Assignee: NATIONAL UNIVERSITY CORPORATION SAITAMA UNIVERSITY, Saitama (JP)

( * ) Notice: Subject to any disclaimer, the term of this patent is extended or adjusted under 35 U.S.C. 154(b) by 792 days.

(21) Appl. No.: 16/335,344

(22) PCT Filed: Sep. 26, 2017

(86) PCT No.: PCT/JP2017/034621
§ 371 (c)(1),
(2) Date: Mar. 21, 2019

(87) PCT Pub. No.: WO2018/056454
PCT Pub. Date: Mar. 29, 2018

(65) Prior Publication Data
US 2019/0276735 A1      Sep. 12, 2019

(30) Foreign Application Priority Data

Sep. 26, 2016   (JP) .............................. JP2016-186496

(51) Int. Cl.
*C08F 2/44*       (2006.01)
*C08F 212/08*     (2006.01)
(Continued)

(52) U.S. Cl.
CPC .............. *C08F 212/22* (2020.02); *A61K 9/10* (2013.01); *A61K 47/32* (2013.01); *C08F 2/44* (2013.01);
(Continued)

(58) Field of Classification Search
CPC .... C08F 212/22; C08F 212/08; C08F 212/36; C08F 2/44; C08F 230/085; C08K 5/14;
(Continued)

(56) References Cited

U.S. PATENT DOCUMENTS 8,735,177 B2 * 5/2014 Sakuma ............. A61K 49/0002
                                                    436/528
10,139,389 B2 * 11/2018 Moore ................... G01N 31/22
(Continued)

FOREIGN PATENT DOCUMENTS

CN        104017129 A      9/2014
CN        104892815 A      9/2015
(Continued)

OTHER PUBLICATIONS

Cao et al. "A green miniemulsion-based synthesis of polymeric aggregation-induced emission nanoparticles", Polymer Chemistry (2015), 6(35), pp. 6378-6385 (Year: 2015).*
(Continued)

*Primary Examiner* — Michael M. Bernshteyn
(74) *Attorney, Agent, or Firm* — Wenderoth, Lind & Ponack, L.L.P.

(57) ABSTRACT

It is an object of the present invention to provide a fine fluorescent particle, which does not cause concentration quenching and has low ecotoxicity. Specifically, the present invention relates to a fine fluorescent particle containing an AIE-active compound, the particle consisting of a network polymer, wherein the fine fluorescent particle is character-
(Continued)

ized in that the AIE-active compound is, for example, a compound represented by the following formula (1):

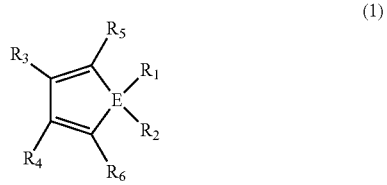

(1)

wherein E represents silicon or germanium; $R_1$ and $R_2$, which are the same or different, each represent a hydrocarbon group containing 1 to 6 carbon atoms, or a substituted or unsubstituted phenyl group; and $R_3$, $R_4$, $R_5$ and $R_6$, which are the same or different, each represent a substituted or unsubstituted phenyl group.

10 Claims, 6 Drawing Sheets

(51) Int. Cl.

| | |
|---|---|
| *C08F 212/36* | (2006.01) |
| *C08K 5/14* | (2006.01) |
| *C09K 11/06* | (2006.01) |
| *C08K 5/54* | (2006.01) |
| *A61K 9/10* | (2006.01) |
| *C08L 25/08* | (2006.01) |
| *A61K 47/32* | (2006.01) |
| *C08F 212/14* | (2006.01) |
| *C08K 5/549* | (2006.01) |
| *A61B 5/00* | (2006.01) |
| *B82Y 15/00* | (2011.01) |
| *C08L 9/00* | (2006.01) |
| *C08F 230/08* | (2006.01) |

(52) U.S. Cl.
CPC .......... *C08F 212/08* (2013.01); *C08F 212/36* (2013.01); *C08K 5/14* (2013.01); *C08K 5/549* (2013.01); *C08L 25/08* (2013.01); *C09K 11/06* (2013.01); *A61B 5/0071* (2013.01); *B82Y 15/00* (2013.01); *C08F 230/085* (2020.02); *C08L 9/00* (2013.01); *C09K 2211/1441* (2013.01)

(58) Field of Classification Search
CPC ................ C08K 5/549; C09K 11/06; C09K 2211/1441; A61K 9/10; A61K 47/32; C08L 26/08; C08L 9/00
USPC .................................................. 252/301.35
See application file for complete search history.

(56) References Cited

U.S. PATENT DOCUMENTS

| | | | |
|---|---|---|---|
| 2009/0075301 A1 | 3/2009 | Sakuma et al. | |
| 2016/0169920 A1 | 6/2016 | Fukushima et al. | |
| 2017/0168037 A1* | 6/2017 | Moore | ............... C08G 18/6225 |
| 2017/0281782 A1* | 10/2017 | Suzuki | ............... A61K 38/1732 |
| 2020/0181486 A1* | 6/2020 | Iwamoto | ............ G01N 33/54386 |

FOREIGN PATENT DOCUMENTS

| | | | |
|---|---|---|---|
| JP | 2010-112777 A | | 5/2010 |
| JP | 2011-180018 A | | 9/2011 |
| JP | 2012185041 A | * | 9/2012 |
| JP | 2015-101543 A | | 6/2015 |
| JP | 2016-158587 A | | 9/2016 |
| JP | 2016-199751 A | | 12/2016 |
| WO | 2007/097318 A1 | | 8/2007 |
| WO | 2015/015844 A1 | | 2/2015 |
| WO | 2016/084979 A1 | | 6/2016 |
| WO | 2017/178882 A1 | | 10/2017 |

OTHER PUBLICATIONS

Wu et al. "Enhancement of Aggregation-Induced Emission in Dye-Encapsulating Polymeric Micelles for Bioimaging", Advanced Functional Materials (2010), 20(9), pp. 1413-1423 (Year: 2010).*
International Search Report dated Dec. 5, 2017, issued in counterpart International Application No. PCT/JP2017/034621 (2 pages).
Cao et al., "Bright and biocompatible AIE polymeric nanoparticles prepared from miniemulsion for fluorescence cell imaging", Polym. Chem., (2016), 7, pp. 5571-5578. (8 pages).
Zhou et al., "Aggregation induced emission based fluorescence pH and temperature sensors: probing polymer interactions in poly(N-isopropyl acrylamide-co-tetra (phenyl) ethene acrylate) /poly (methacrylic acid) interpenetrating polymer networks," Journal of Materials Chemistry C: Materials for Optical and Electronic Devices, (2015), 3 (21), pp. 5490-5498. (9 pages).
Liu et al., "Hyperbranched conjugated polysiloles: synthesis, structure, aggregation-enhanced emission, Multicolor Fluorescent Photopatterning, and Superamplined Detection of Explosives," Macromolecules, (Jun. 28, 2010), 43 (11), pp. 4921-4936. (16 pages).

* cited by examiner

[Figure 1]
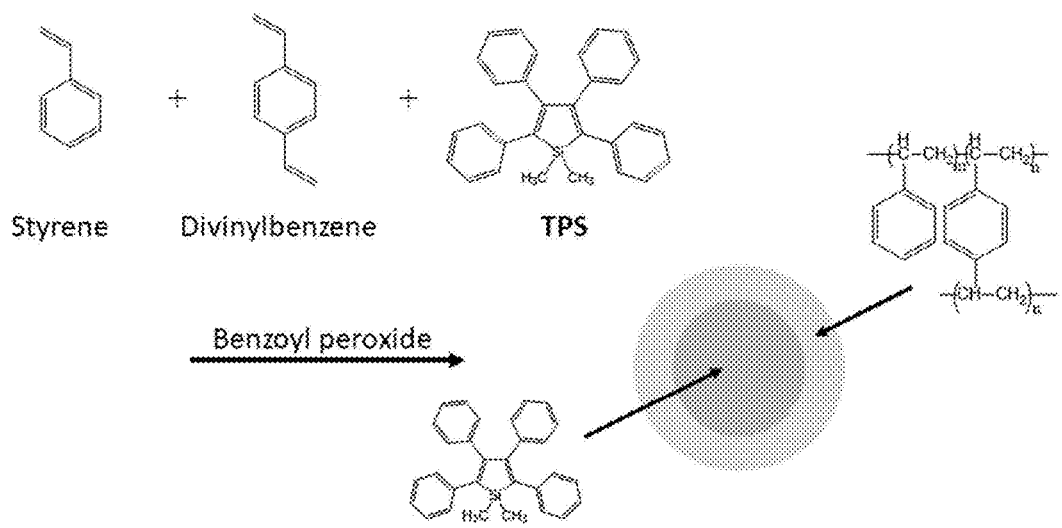
[Figure 2]
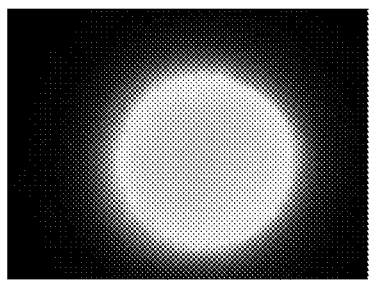
Photographing conditions
Excitation wavelength: 330 - 380 nm
Exposure time: 200 msec
Gain: 1.00x   : 1.00×

[Figure 3]
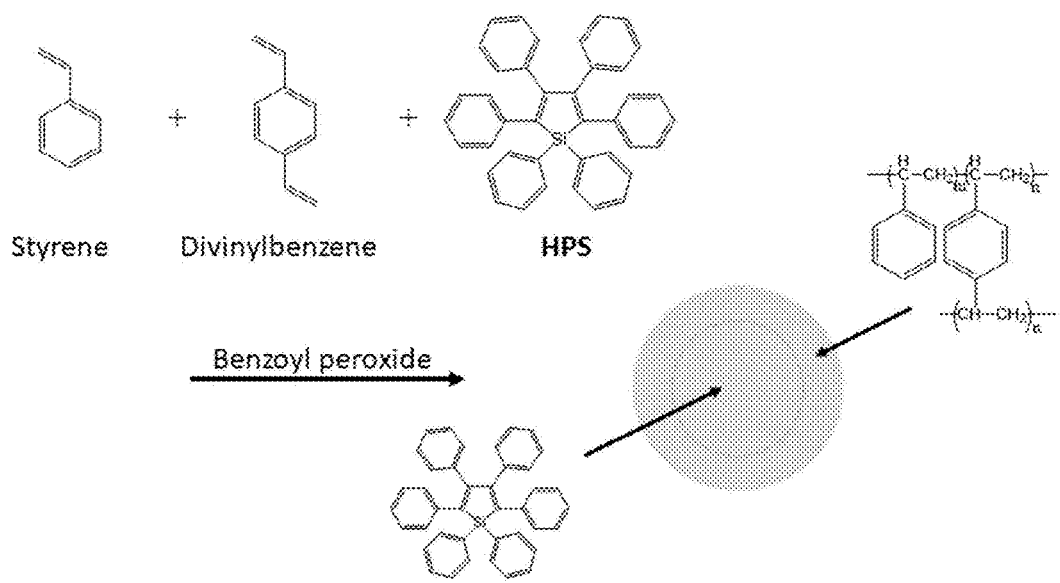
[Figure 4]
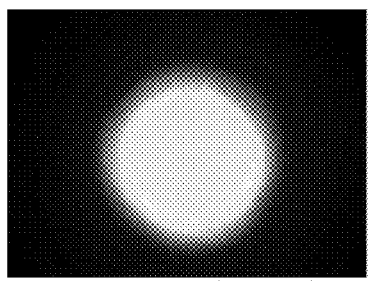
Photographing conditions
   Excitation wavelength: 380 - 420 nm
   Exposure time: 200 msec
   Gain: 1.00x

[Figure 5]
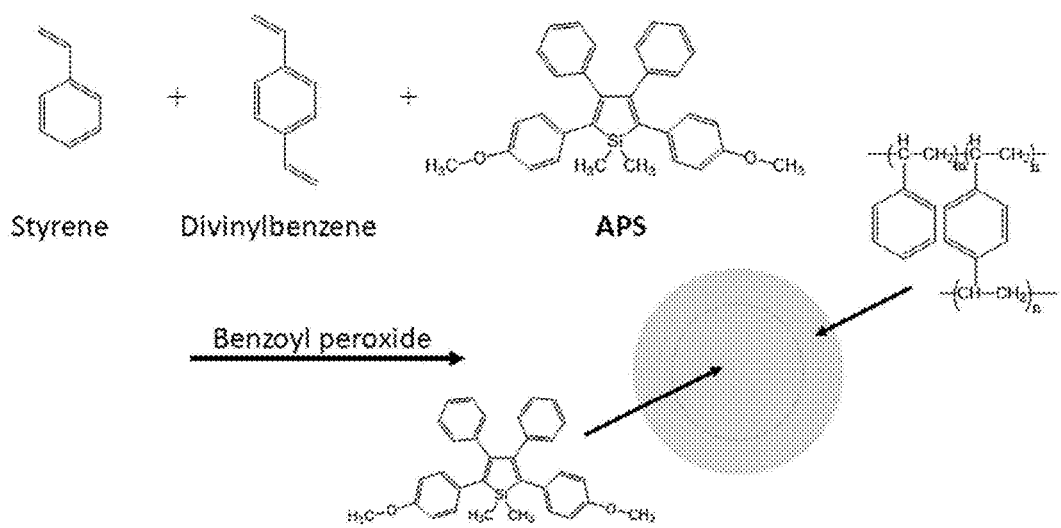
Styrene    Divinylbenzene    APS
Benzoyl peroxide →
[Figure 6]
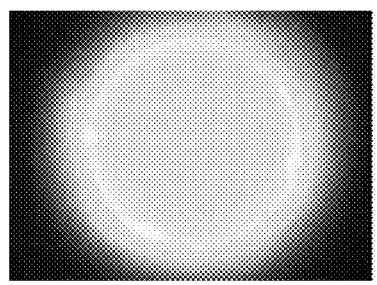
Photographing conditions
   Excitation wavelength: 380 - 420 nm
   Exposure time: 200 msec
   Gain: 1.00x

[Figure 7]
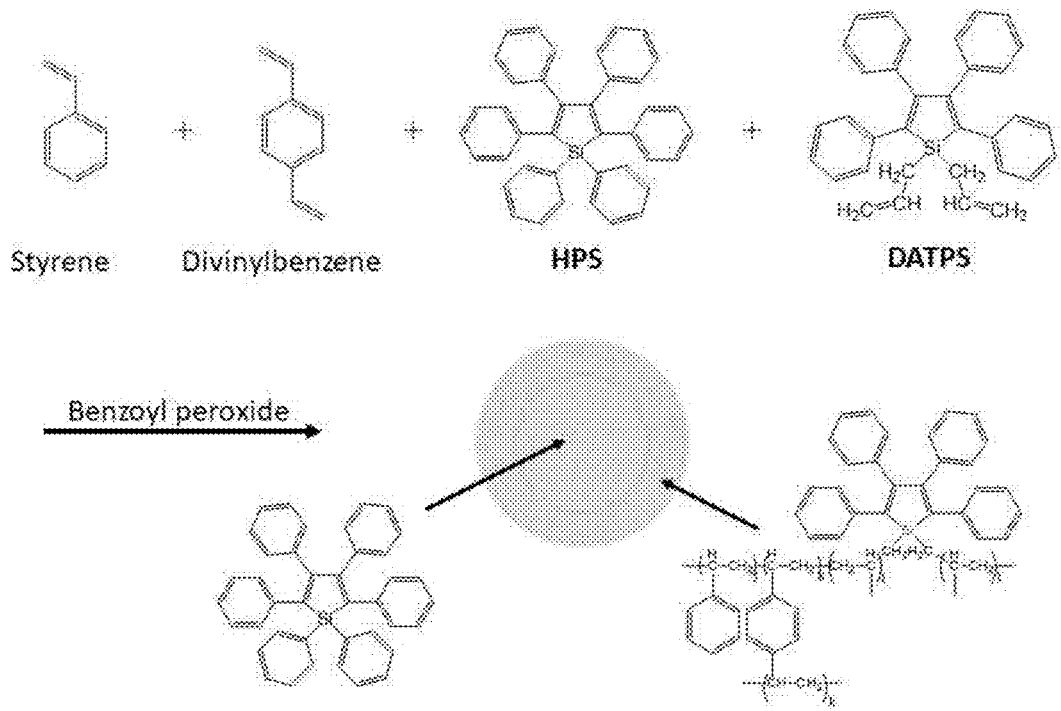
[Figure 8]
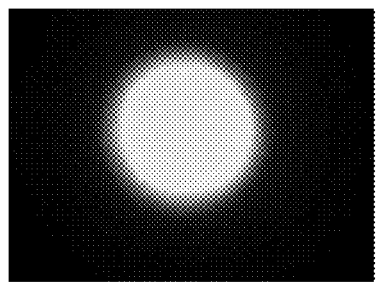
Photographing conditions
   Excitation wavelength: 380 - 420 nm
   Exposure time: 200 msec
   Gain: 1.00x

[Figure 9]
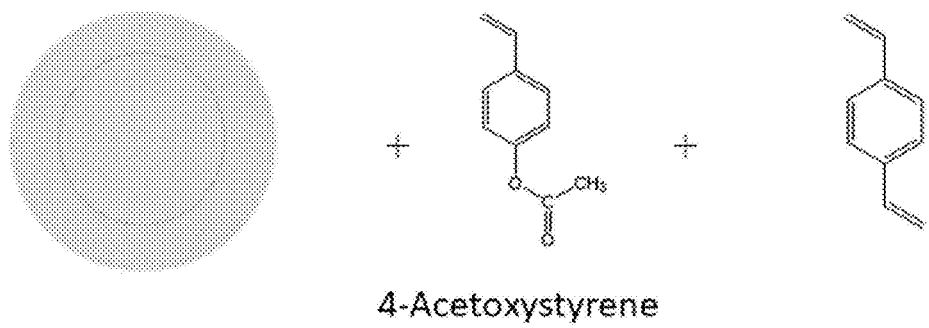
4-Acetoxystyrene
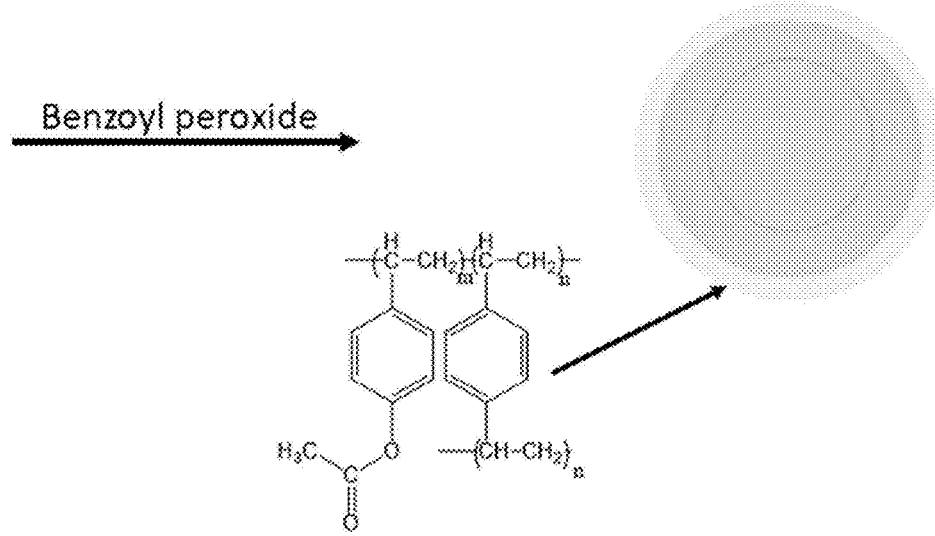
[Figure 10]
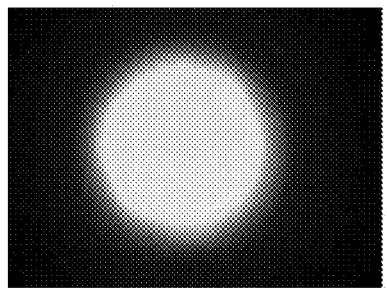
Photographing conditions
 Excitation wavelength: 330 - 380 nm
 Exposure time: 200 msec
 Gain: 1.00x

[Figure 11]
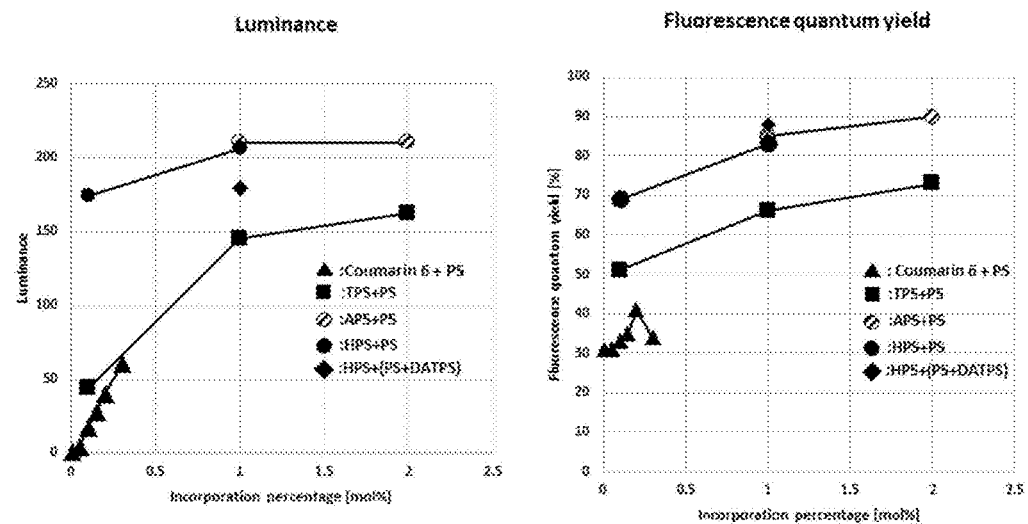
[Figure 12]
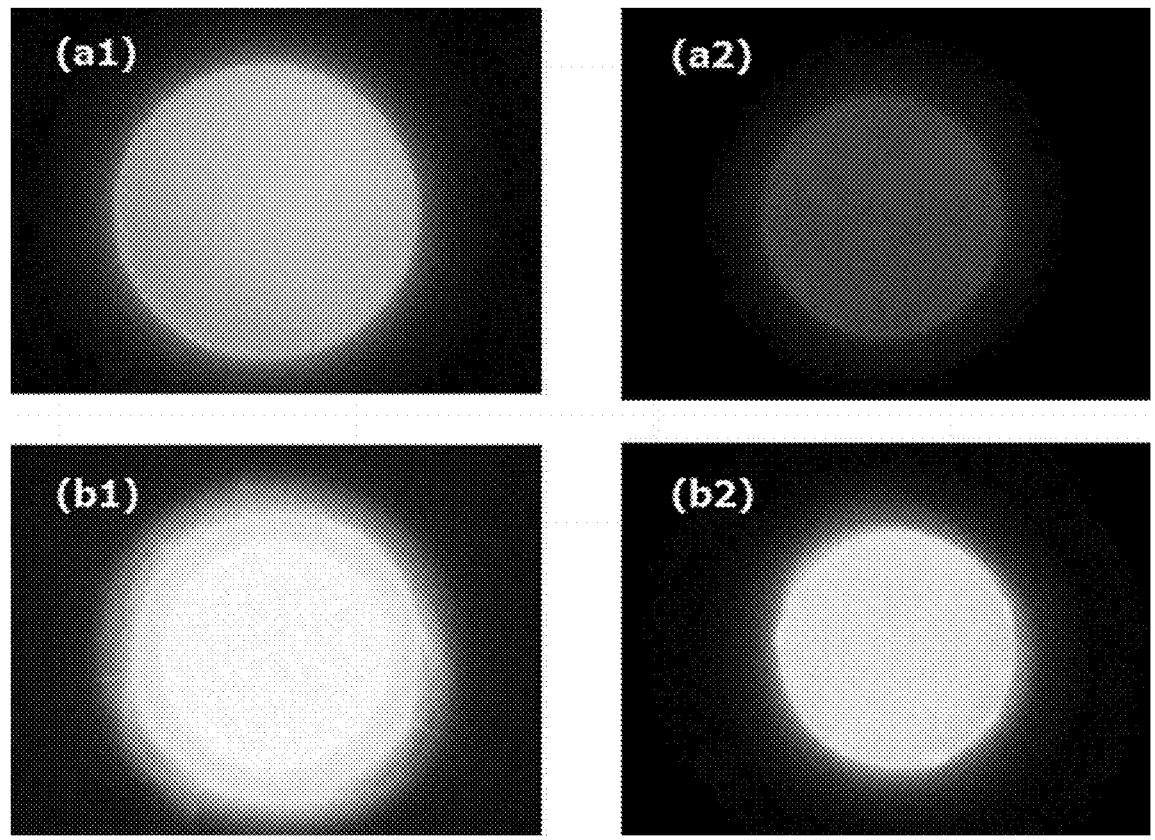

FINE FLUORESCENT PARTICLE CONTAINING AIE-ACTIVE COMPOUND

TECHNICAL FIELD

The present invention relates to a fine fluorescent particle containing an AIE-active compound.

BACKGROUND ART

When a fine fluorescent particle is allowed to bind to a target recognizing substance such as an antibody, it can fluorescently label a target substance. For example, such a fine fluorescent particle is allowed to bind to an antibody that recognizes a molecule specifically binding to the surface of a cancer cell, and the resulting antibody is then used as a probe to examine the presence or absence of a cancer cell in a test sample, so that a possibility of being affected with cancer can be diagnosed. Moreover, even in bioimaging that is a technique of imaging the distribution or localization of biomolecules such as proteins at the level of a cell, a tissue, or an individual body, the fine fluorescent particle is utilized in the fluorescent labeling of a probe.

Among others, with regard to a fine fluorescent particle formed by incorporating an organic fluorescent substance into a polymeric resin, several products having a different color, size and surface modification are commercially available, and the usefulness thereof has been approved in the field of biology and medical research, and also in the field of clinical medicine such as diagnosis (Patent Literature 1 and Patent Literature 2).

A majority of known fluorescent substances, which are incorporated into fine fluorescent particles, are highly planar compounds with an extended π-conjugated system. It has been known that, when such a compound is used in a high concentration, it causes "concentration quenching," by which emission intensity is drastically reduced. As such, the amount of fluorescent substances that can be incorporated into a polymeric resin has a certain limit. The present inventors have actually confirmed that such concentration quenching takes place in commercially available products.

When the amount of a target to be labeled is small, in order to effectively detect the target, it is preferable to use a fine fluorescent particle that is as bright as possible, and thus, it is necessary to use a fine fluorescent particle, in which the amount of a fluorescent substance per unit incorporated into a polymeric resin is as large as possible. However, the amount of the conventional fluorescent substance that can be incorporated into a molecular resin has a certain limit. Accordingly, as long as the conventional fluorescent substance is used, the brightness of the produced fine fluorescent particles also has a certain limit.

A quantum dot is used for the same intended use as that of the fine fluorescent particle. However, since a highly toxic element such as cadmium or selenium is used in the quantum dot, the quantum dot is not suitable for use in vivo. In addition, since the fluorescence yield of the quantum dot is not so high (up to 50%), it is also problematic in terms of brightness.

CITATION LIST

Patent Literature

Patent Literature 1: WO2007/097318
Patent Literature 2: JP Patent Publication (Kokai) No. 2015-101543 A
Patent Literature 3: JP Patent Publication (Kokai) No. 2010-112777 A
Patent Literature 4: JP Patent Publication (Kokai) No. 2011-180018 A
Patent Literature 5: JP Patent Publication (Kokai) No. 2016-158587 A

Non Patent Literature

Non Patent Literature 1: Cao et al., Polym. Chem. 7: 5571-5578, 2016

SUMMARY OF INVENTION

Technical Problem

Taking into consideration the aforementioned circumstances, it is an object of the present invention to provide a fine fluorescent particle, which does not cause concentration quenching and has high luminance and low ecotoxicity.

Solution to Problem

To date, the present inventors had developed a method for detecting various bacteria or viruses, using a substance having AIE (Aggregation-Induced Emission) activity (wherein "AIE" indicates a phenomenon by which molecules, in which multiple aryl groups and the like bind to one another such that they surround a ring in the center, aggregate with one another and emit fluorescence with high efficiency by ultraviolet irradiation) (Patent Literatures 3 to 5). The present inventors have further conducted studies based on accumulated findings regarding the AIE phenomenon. As a result, the inventors have found that, when a substance having AIE activity is used as an organic fluorescent substance to be incorporated into a polymeric resin, the resulting resin does not cause concentration quenching, and rather, when such a substance having AIE activity is used in a high concentration, the resulting resin has extremely high luminous efficiency.

Recently, a fine fluorescent particle, which utilizes a molecule having AIE activity (AIE molecule) as a polymerizable monomer and allows the AIE molecule to covalently bind to a polymeric resin, has been reported (Non Patent Literature 1). On the other hand, the fine fluorescent particle of the present invention is different from the fine particle disclosed in Non Patent Literature 1, in that an AIE molecule does not covalently bind to a polymeric resin but is simply contained in the polymeric resin (i.e., is incorporated into the polymeric resin). Moreover, since the AIE molecule is not detained by the polymeric resin (i.e., does not covalently bind to the polymeric resin) in the fine fluorescent particle of the present invention, the present fine fluorescent particle is advantageous in that the AIE molecules aggregate with one another more easily than the AIE molecules in the fine particle disclosed in Non Patent Literature 1, and thus, higher luminance can be achieved.

The present inventors have used silole as a substance having AIE activity to produce fine polystyrene particles, in which 2.0 mol % silole is incorporated. Then, the inventors have confirmed that, in comparison in terms of luminance, the thus produced fine polystyrene particles emit the light more brightly than resins serving as commercially available products.

That is to say, the present invention relates to a fine fluorescent particle containing an AIE-active compound (a compound having AIE activity) (which comprises an AIE compound that, at least, does not covalently bind to a polymer), wherein the particle consists of a network polymer.

Advantageous Effects of Invention

When compared with an existing fine fluorescent particle having an equivalent particle diameter, the fine fluorescent particle of the present invention has properties that are high luminance and high fluorescence quantum yield.

Moreover, with regard to the fine fluorescent particle of the present invention, since a majority of AIE-active compounds, which are incorporated into a polymeric resin, have low biological toxicity, the present fine fluorescent particle can be used in bioimaging in vivo.

Since the fine fluorescent particle of the present invention is brighter than existing fine fluorescent particles, even if the amount of a target to be labeled (e.g., cancer cells, etc.) is small, the target can be effectively detected.

BRIEF DESCRIPTION OF DRAWINGS

FIG. 1 is a scheme for synthesizing a fine polystyrene particle containing 1,1-dimethyl-2,3,4,5-tetraphenylsilole.

FIG. 2 is a fluorescence micrograph showing a fine polystyrene particle containing 1,1-dimethyl-2,3,4,5-tetraphenylsilole.

FIG. 3 is a scheme for synthesizing a fine polystyrene particle containing 1,1,2,3,4,5-hexaphenylsilole.

FIG. 4 is a fluorescence micrograph showing a fine polystyrene particle containing 1,1,2,3,4,5-hexaphenylsilole.

FIG. 5 is a scheme for synthesizing a fine polystyrene particle containing 1,1-dimethyl-2,5-dianisyl-3,4-diphenylsilole.

FIG. 6 is a fluorescence micrograph showing a fine polystyrene particle containing 1,1-dimethyl-2,5-dianisyl-3,4-diphenylsilole.

FIG. 7 is a scheme for synthesizing a fine polystyrene particle containing 1,1,2,3,4,5-hexaphenylsilole. As crosslinkers, divinylbenzene and 1,1-diallyl-2,3,4,5-tetraphenylsilole were used.

FIG. 8 is a fluorescence micrograph showing a fine polystyrene particle containing 1,1,2,3,4,5-hexaphenylsilol. As crosslinkers, divinylbenzene and 1,1-diallyl-2,3,4,5-tetraphenylsilole were used.

FIG. 9 is a synthetic scheme for coating the surface of a fine polystyrene particle containing 1,1,2,3,4,5-hexaphenylsilole with polyacetoxystyrene.

FIG. 10 is a fluorescence micrograph showing a fine polystyrene particle containing 1,1,2,3,4,5-hexaphenylsilole, the surface of which is modified with a hydroxy group.

FIG. 11 shows a comparison made in terms of luminance and fluorescence quantum yield, among a case where a polystyrene network polymer was allowed to contain coumarin 6 that is a highly planar fluorescent compound having an extended π-conjugated system ("coumarin 6+PPS" in the figure), a case where a polystyrene network polymer was allowed to contain TPS ("TPS+PS" in the figure), HPS ("HPS+PS" in the figure) or APS ("APS+PS" in the figure), a case where DATPS was incorporated as a monomer into a network polymer and HPS was then added to the network polymer ("HPS+(PS+DATPS)" in the figure). "PS" indicates a polystyrene polymer.

FIG. 12 includes fluorescence micrographs showing fine particles containing coumarin 6 in a polystyrene network polymer thereof (a1 and a2), and fine particles containing 1,1,2,3,4,5-hexaphenylsilole in a polystyrene network polymer thereof. The exposure time is 1 sec in the case of a1 and b1, whereas the exposure time is 200 msec in the case of a2 and b2.

DESCRIPTION OF EMBODIMENTS

A first embodiment of the present invention relates to a fine fluorescent particle containing an AIE-active compound, wherein the particle consists of a network polymer (hereafter referred to as "the fine fluorescent particle of the present invention").

The AIE-active compound contained in the fine fluorescent particle of the present invention is not particularly limited, and it may be any compound. Examples of the AIE-active compound used herein include the compounds disclosed in Patent Literatures 3 to 5, and the compounds disclosed in JP Patent Publication (Kokai) No. 2013-163767 A, JP Patent Publication (Kokai) No. 2014-12654 A, JP Patent Publication (Kokai) No. 2015-30820 A, or U.S. Pat. No. 8,134,017B.

A more specific example of the AIE-active compound usable in the first embodiment may be, for example, a compound represented by the following formula (1):

[Formula 1]

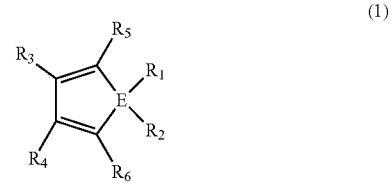

(1)

In the above formula (1), E represents silicon or germanium, and preferably represents silicon.

$R_1$ and $R_2$, which are the same or different, each represent a hydrocarbon group containing 1 to 6 carbon atoms, or a substituted or unsubstituted phenyl group, and preferably each represent a methyl group or a substituted or unsubstituted phenyl group.

$R_3$, $R_4$, $R_5$ and $R_6$, which are the same or different, each represent a substituted or unsubstituted phenyl group; preferably each represent any one of p-$((CH_3)_2N)C_6H_4$, p-$CH_3OC_6H_4$, p-$CH_3C_6H_4$, $C_6H_5$, p-$F_3CC_6H_4$, p-$(NO_2)C_6H_4$, m-$CH_3C_6H_4$, m-$FC_6H_4$, m-$F_3CC_6H_4$, 1-naphthyl, 2-styryl, biphenyl, 2-thienyl, bithienyl, 5-(2-benzo[b]thienyl)2-thienyl, 2-thiazole, 2-pyridyl, 3-pyridyl, N-methyl-2-pyrrolyl, 2,4,6-trimethylphenyl (Mes), or 2,4,6-triisopropylphenyl (Tip); and particularly preferably each represent a phenyl group ($C_6H_5$) or a p-methoxyphenyl group (p-$CH_3OC_6H_4$).

The network polymer according to the first embodiment (hereafter referred to as "the network polymer of the present invention") means a polymeric compound, which is capable of forming a three-dimensional network structure as a result of the crosslinking of polymers, and containing (incorporating) a fluorescent molecule or the like in the structure thereof. The network polymer may be, for example, the following styrene-based polymer:

[Formula 2]

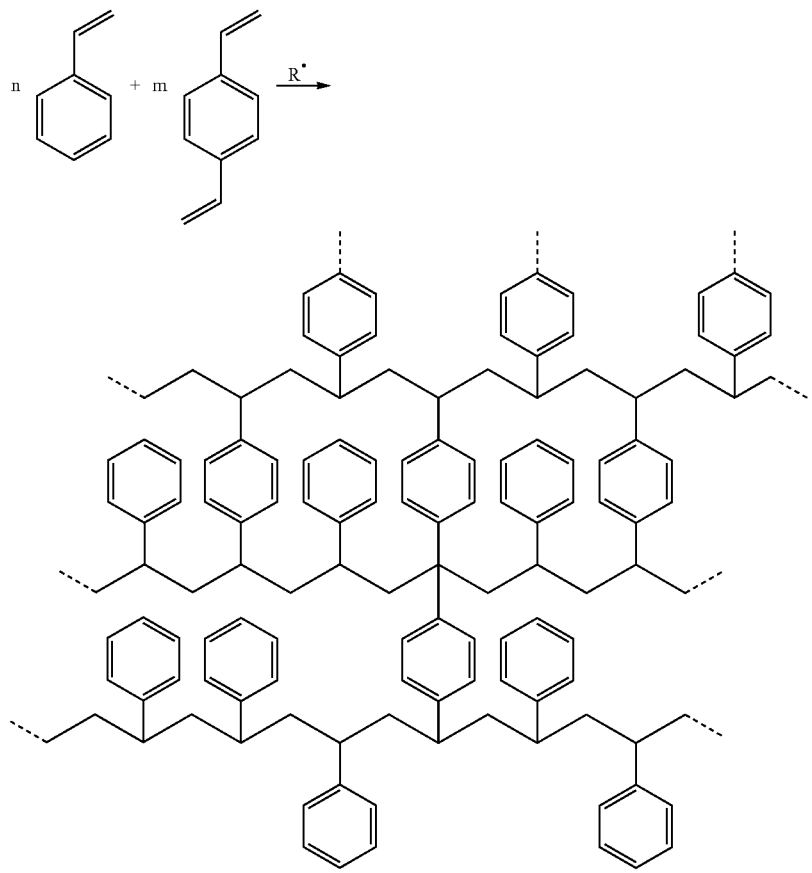

The size of the fine particle of the present invention is not particularly limited, and it can be freely selected depending on the purpose of use. For example, the particle diameter of the present fine particle is 1 nm to 500 μm, 1 nm to 100 μm, or 10 nm to 20 μm, preferably 10 nm to 500 nm, more preferably 10 nm to 200 nm, and further preferably 10 nm to 100 nm.

The network polymer of the present invention is not particularly limited, and it may be, for example, a vinyl polymer crosslinked by a diene. The aforementioned vinyl polymer may be synthesized by using, as a monomer(s), one or more (2 or 3) selected from among, for example, substituted or unsubstituted styrene (e.g., styrene, p-methoxystyrene, α-methylstyrene, acetoxy styrene, etc.), vinyl acetate, vinyl chloride, acrylonitrile, methacrylonitrile, vinylidene cyanide, propylene, isobutene, N-vinylcarbazole, methyl vinyl ketone, vinylpyridine, nitroethylene, acrylic acid ester (e.g., methyl acrylate, ethyl acrylate, (n-, i-, or t-)butyl acrylate, 2-ethylhexyl acrylate, 2-dimethylaminoethyl acrylate, 2-hydroxyethyl acrylate, etc.), methacrylic acid ester (e.g., methyl methacrylate, ethyl methacrylate, (n-, i-, or t-)butyl methacrylate, 2-ethylhexyl methacrylate, etc.), cyanoacrylic acid ester (2-cyanomethyl acrylate, 2-cyanoethyl acrylate, 3-cyanobutyl acrylate, etc.), and vinyl ether.

In addition, examples of the diene that crosslinks the above-described vinyl polymer include isoprene, butadiene, and divinylbenzene.

Moreover, as a monomer constituting the above-described vinyl polymer, an AIE-active compound having an alkenyl group may be selected. In this case, since such an AIE-active compound is not only contained in the network polymer, but is also contained on the surface of the network polymer, it becomes possible to produce a further brighter fine fluorescent particle. As such an AIE-active compound having an alkenyl group, a monomer represented by the following formula (2) can be used, for example:

[Formula 3]

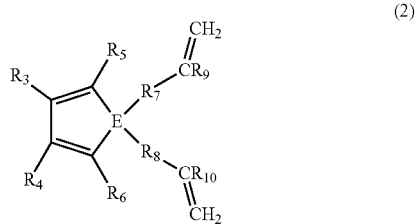

(2)

In the above formula (2), E represents silicon or germanium, and preferably represents silicon.

$R_3$, $R_4$, $R_5$ and $R_6$, which are the same or different, each represent a substituted or unsubstituted phenyl group; preferably each represent any one of p-$((CH_3)_2N)C_6H_4$, p-$CH_3OC_6H_4$, p-$CH_3C_6H_4$, $C_6H_5$, p-$F_3CC_6H_4$, p-$(NO_2)C_6H_4$, m-$CH_3C_6H_4$, m-$FC_6H_4$, m-$F_3CC_6H_4$, 1-naphthyl, 2-styryl, biphenyl, 2-thienyl, bithienyl, 5-(2-benzo[b]thienyl)2-thienyl, 2-thiazole, 2-pyridyl, 3-pyridyl, N-methyl-2-pyrrolyl, 2,4,6-trimethylphenyl (Mes), or 2,4,6-triisopropylphenyl (Tip); and particularly preferably each represent a phenyl group ($C_6H_5$) or a p-methoxyphenyl group (p-$CH_3OC_6H_4$).

$R_7$ and $R_8$, which are the same or different, each represent a hydrocarbon chain containing 1 to 6 carbon atoms, or an aryl group, and preferably each represent a methyl chain, an ethyl chain, or a benzene chain.

$R_9$ and $R_{10}$, which are the same or different, each represent hydrogen or an alkyl group containing 1 to 6 carbon atoms (e.g., a methyl group, an ethyl group, or a propyl group), and preferably each represent hydrogen.

A specific example of the network polymer of the first embodiment may be, for example, a styrene-based polymer, in which a polymer represented by the following formula (3) is crosslinked by a diene (e.g., divinylbenzene):

[Formula 4]

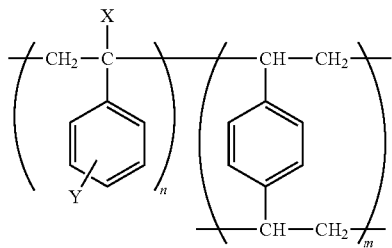

(3)

In the above formula (3), X represents hydrogen, a hydrocarbon group containing 1 to 6 carbon atoms (e.g., a methyl group, an ethyl group, a propyl group, etc.) or the like, and preferably represents hydrogen or a methyl group. In the above formula (3), Y represents hydrogen, an alkoxy group containing 1 to 6 carbon atoms (e.g., a methoxy group or an ethoxy group), an alkyl group containing 1 to 6 carbon atoms (e.g., an alkyl group or an ethyl group), an acyl group containing 1 to 6 carbon atoms (e.g., a formyl group, a propionyl group, or a butyryl group), a carboxylate group containing 1 to 6 carbon atoms (e.g., an acetoxy group) or the like, and preferably represents hydrogen, a methoxy group, or an acetoxy group. Moreover, the position at which Y binds to a benzene ring is not particularly limited, and it may be any one of the para position, the meta position, and the ortho position.

Furthermore, n and m each represent an integer, and with regard to the ratio between n and m, n:m=1:0.2 to 2, and preferably n:m=1:0.5.

Further, when an AIE-active compound is used as a monomer constituting a network polymer, a specific example of the network polymer may be a polymer represented by the following formula (4) that is crosslinked by a diene (e.g., divinylbenzene):

[Formula 5]

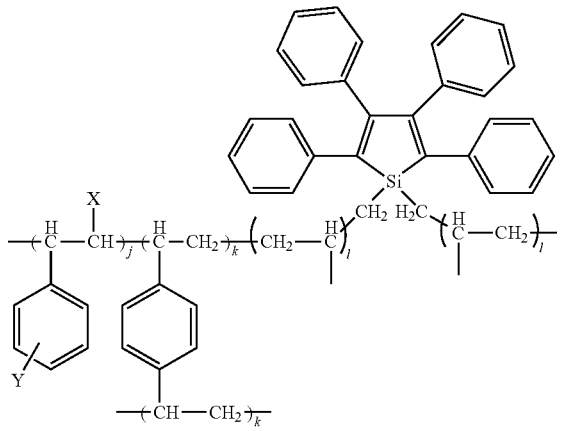

(4)

In the above formula (4), X represents hydrogen, an alkyl group containing 1 to 6 carbon atoms (e.g., a methyl group, an ethyl group, a propyl group, or hydrogen) or the like, and preferably represents hydrogen or a methyl group. In the above formula (4), Y represents hydrogen, an alkoxy group containing 1 to 6 carbon atoms (e.g., a methoxy group or an ethoxy group), an alkyl group containing 1 to 6 carbon atoms (e.g., an alkyl group or an ethyl group), an acyl group containing 1 to 6 carbon atoms (e.g., a formyl group, a propionyl group, or a butyryl group), a carboxylate group containing 1 to 6 carbon atoms (e.g., an acetoxy group) or the like, and preferably represents hydrogen, a methoxy group, or an acetoxy group. Moreover, the position at which Y binds to a benzene ring is not particularly limited, and it may be any one of the para position, the meta position, and the ortho position.

Furthermore, j, k, and l each represent an integer, and with regard to the ratio among j, k, and l, j:k:l=1:0.2 to 2:0.01 to 0.1, and preferably j:k:l=1:0.5:0.02.

Further, the fine fluorescent particle of the present invention may be allowed to bind to an antibody or a ligand molecule binding to a specific molecule (e.g., an antibody, a ligand and the like specifically binding to a cancer marker, etc.), so that it can be used as a fluorescent label. In this case, it may also be possible to perform a treatment of allowing a functional group, a molecule, an atom or the like (e.g., a hydroxyl group, an amino group, a maleimide group, halogen, an ester, a carboxyl group, etc.) to appear on the surface of a network polymer structure, wherein the aforementioned functional group, molecule, atom or the like serves as a scaffold for binding a ligand molecule or the like, such as an antibody, a protein or a lipid, onto the surface of the fine fluorescent particle of the present invention (i.e., the network polymer structure).

The method of enclosing (encapsulating or incorporating) an AIE-active compound into a particle consisting of a network polymer is not particularly limited, as long as it is a method in which the AIE-active compound is not eluted from the network polymer structure. For example, it may be a method of allowing an AIE-active compound to co-exist in a synthetic system in a process of synthesizing a network polymer, so that the network polymer is synthesized and at the same time, the AIE-active compound is incorporated into the synthesized network polymer.

The method for producing the fine fluorescent particle of the present invention will be described below, exemplifying the case of using a styrene-based polymer as a network polymer.

[Formula 6]

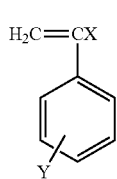

(5)

The styrene derivative represented by the above formula (5) (wherein Y represents hydrogen, an alkoxy group containing 1 to 6 carbon atoms (e.g., a methoxy group or an ethoxy group), an alkyl group containing 1 to 6 carbon atoms (e.g., an alkyl group or an ethyl group), an acyl group containing 1 to 6 carbon atoms (e.g., a formyl group, a propionyl group, or a butyryl group), a carboxylate group containing 1 to 6 carbon atoms (e.g., an acetoxy group) or the like, and preferably represents hydrogen, a methoxy group, or an acetoxy group, and further, the position at which Y binds to a benzene ring is not particularly limited, and it may be any one of the para position, the meta position, and the ortho position) is mixed with divinylbenzene serving as a crosslinking compound, and the mixture is then polymerized in a polar solvent or in a non-polar solvent. For example, when the number of moles of the monomer as shown in the formula (3) is defined as m and the number of moles of the divinylbenzene is defined as n, the two substances are mixed at a ratio of m:n=1:0.2 to 2, for example, in a polar solvent.

As a solvent used in the polymerization reaction, a polar solvent such as water, or a non-polar solvent such as toluene is preferable. Otherwise, a polymerization reaction using the monomer itself as a solvent (a radical polymerization reaction, etc.) may also be carried out.

The polymerization reaction can be carried out under conditions, which can be easily selected by a person skilled in the art. For instance, using benzoyl peroxide, azobisisobutyronitrile, potassium peroxodisulfate, or t-butyl hydroperoxide as a catalyst (polymerization initiator), the reaction can be carried out for approximately 1 hour to 24 hours, under reaction temperature conditions such as 40° C. to 100° C.

The particle diameter of a network polymer to be prepared is different depending on the mixing ratio between the used monomer and crosslinking compound and the type of a solvent used. The particle diameter is within the range of approximately 10 nm to 200 μm.

Further, in order to allow the network polymer to comprise an AIE-active compound, as mentioned above, the AIE-active compound is allowed to co-exist in a synthetic system in the process of synthesizing the network polymer, so that the AIE-active compound can be incorporated into the network polymer.

The contents disclosed in all publications cited in the present description are incorporated herein by reference in their entirety. In addition, throughout the present description, when singular terms such as "a," "an," and "the" are used, these terms include not only single items but also multiple items, unless otherwise clearly specified in the context.

Hereinafter, the present invention will be further described in the following examples. However, these examples are only examples of the embodiments of the present invention, and thus, the examples are not intended to limit the scope of the present invention.

Examples

1. Synthesis of Fine Polystyrene Particles Containing 1,1-dimethyl-2,3,4,5-tetraphenylsilole (Crosslinker: Divinylbenzene)

1,1-Dimethyl-2,3,4,5-tetraphenylsilole (TPS) (26.2 mg, 0.064 mmol) and benzoyl peroxide having a purity of 75% (10.2 mg, 0.032 mmol) were dissolved in a mixed solution of styrene (251 mg, 2.41 mmol) and divinylbenzene (120 mg, 0.92 mmol).

Specifically, the inside of a two-necked eggplant flask equipped with an argon balloon, an Allihn condenser, a three-way cock and a septum was replaced with argon, and thereafter, 20 mL of a polyvinyl alcohol aqueous solution that had been prepared to a concentration of 1 g/L was added into the flask. While stirring the aqueous solution, the previously prepared monomer was added dropwise thereto (FIG. 1). After the reaction mixture had been fully dispersed, the inside of the synthetic system was kept at 80° C., and a polymerization reaction was carried out for 3 hours. After completion of the reaction, the solvent was removed by decantation, and the residue was then subjected to a heat treatment with distilled water at 80° C. and then, to washing with methanol. The obtained fine particles were dried under reduced pressure to obtain 80.3 mg of a product of interest (yield: 22%) (FIG. 2).

Besides, TPS was synthesized as shown in the following scheme 1.

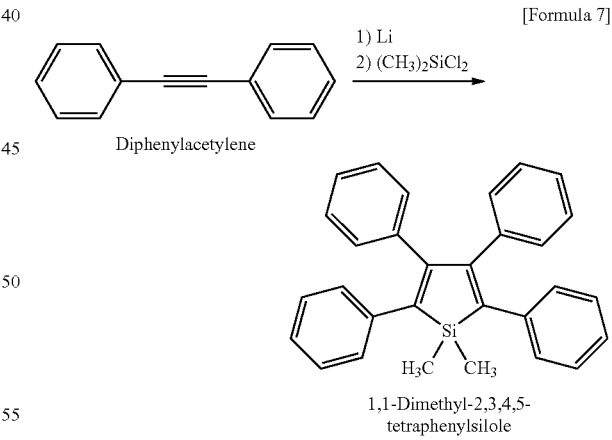

Scheme 1

[Formula 7]

1,1-Dimethyl-2,3,4,5-tetraphenylsilole

Specifically, a two-necked eggplant flask equipped with an argon balloon, a septum and a three-way cock was replaced with argon, and thereafter, diphenylacetylene (2.57 g, 14.4 mmol), lithium (0.200 g, 28.8 mmol) and 16 mL of ether were added into the flask. After that, ultrasonic wave was applied to the flask for 1.5 hours, so that a reaction was initiated. Thereafter, the reaction mixture was stirred at room temperature for 3.5 hours to carry out the reaction. A three-necked flask equipped with an argon balloon, an isobaric dropping funnel, a septum and a three-way cock was replaced with argon, and then, the previously prepared solution was transferred into the flask, using a cannula, under an argon atmosphere. While this reaction system was cooled to −196° C. with liquid nitrogen, a mixed solution of dimethyldichlorosilane (2.23 g, 17.2 mmol) and 16 mL of ether was added dropwise through the isobaric dropping funnel. After completion of the dropwise addition, the reaction system was removed from liquid nitrogen and was then reacted at room temperature for 12 hours. Subsequently, ice and 1 M hydrochloric acid were added to the reaction system to inactivate the reaction. Extraction with ethyl acetate was performed, and thereafter, the extract was successively washed with distilled water and a saturated saline, and was then dried over magnesium sulfate. After the solvent had been distilled away, the residue was purified by silica gel column chromatography using, as an eluent, hexane:ethyl acetate=1:0 to 10:1. Thereafter, the resultant was recrystallized from hexane to obtain 1.158 g of a product of interest (yield: 39%).

2. Synthesis of Fine Polystyrene Particles Containing 1,1,2,3,4,5-hexaphenylsilole (Crosslinker: Divinylbenzene)

1,1,2,3,4,5-Hexaphenylsilole (HPS) (17.2 mg, 0.032 mmol) and benzoyl peroxide having a purity of 75% (10.2 mg, 0.032 mmol) were dissolved in a mixed solution of styrene (251 mg, 2.41 mmol) and divinylbenzene (120 mg, 0.92 mmol).

Specifically, the inside of a two-necked eggplant flask equipped with an argon balloon, an Allihn condenser, a three-way cock and a septum was replaced with argon, and thereafter, 20 mL of a polyvinyl alcohol aqueous solution that had been prepared to a concentration of 1 g/L was added into the flask. While stirring the aqueous solution, the previously prepared monomer was added dropwise thereto (FIG. 3). After the reaction mixture had been fully dispersed, the inside of the synthetic system was kept at 80° C., and a polymerization reaction was carried out for 3 hours. After completion of the reaction, the solvent was removed by decantation, and the residue was then subjected to a heat treatment with distilled water at 80° C. and then, to washing with methanol. The obtained fine particles were dried under reduced pressure to obtain 135 mg of a product of interest (yield: 36%) (FIG. 4).

Besides, HPS was purchased from Tokyo Chemical Industry Co., Ltd.

3. Synthesis of Fine Polystyrene Particles Containing 1,1-dimethyl-2,5-dianisyl-3,4-diphenylsilole (Crosslinker: Divinylbenzene)

1,1-Dimethyl-2,5-dianisyl-3,4-diphenylsilole (APS) (30.4 mg, 0.064 mmol) and benzoyl peroxide having a purity of 75% (10.2 mg, 0.032 mmol) were dissolved in a mixed solution of styrene (251 mg, 2.41 mmol) and divinylbenzene (120 mg, 0.92 mmol).

Specifically, the inside of a two-necked eggplant flask equipped with an argon balloon, an Allihn condenser, a three-way cock and a septum was replaced with argon, and thereafter, 20 mL of a polyvinyl alcohol aqueous solution that had been prepared to a concentration of 1 g/L was added into the flask. While stirring the aqueous solution, the previously prepared monomer was added dropwise thereto (FIG. 5). After the reaction mixture had been fully dispersed, the inside of the synthetic system was kept at 80° C., and a polymerization reaction was carried out for 3 hours. After completion of the reaction, the solvent was removed by decantation, and the residue was then subjected to a heat treatment with distilled water at 80° C. and then, to washing with methanol. The obtained fine particles were dried under reduced pressure to obtain 127 mg of a product of interest (yield: 34%) (FIG. 6).

Besides, APS was synthesized as shown in the following scheme 2.

Specifically, a two-necked eggplant flask equipped with an argon balloon, a septum and a three-way cock was replaced with argon, and thereafter, lithium (0.052 g, 8.0 mmol), naphthalene (1.026 g, 8.0 mmol), and 8 mL of tetrahydrofuran (THF) were added into the flask. After that, ultrasonic wave was applied to the flask for 20 minutes, so that a reaction was initiated. Thereafter, the reaction mixture was stirred at room temperature for 3 hours to prepare lithium naphthalenide. A three-necked eggplant flask equipped with an argon balloon, a coil, a septum, an isobaric dropping funnel and a three-way cock was replaced with argon, and then, the previously prepared solution was transferred into the flask, using a cannula, under an argon atmosphere. After 5 mL of a THF solution of bis(phenylethynyl)dimethylsilane (0.520 g, 2.0 mmol) was added dropwise into the flask through the isobaric dropping funnel, and the obtained mixture was then stirred for 20 minutes. While the inside of this reaction system was cooled to 0° C. with ice water, 10 mL of THF was added thereto. Thereafter, dichloro(N,N,N',N'-tetramethylethylenediamine)zinc(II) (2.020 g, 8.0 mmol) was added to the reaction mixture, the reaction system was then removed from the ice water, and a reaction was then carried out at room temperature for 1 hour. Thereafter, p-bromoanisole (0.786 g, 4.2 mmol), bis(triphenylphosphine)palladium dichloride (0.070 g, 0.1 mmol), and 10 mL of THF were added to the reaction mixture, the inside of the synthetic system was then kept at 65° C., and a reaction was then carried out for 15 hours. Subsequently, 1 M hydrochloric acid was added to the reaction system to inactivate the reaction. Extraction with chloroform was performed, and thereafter, the extract was successively washed with distilled water and a saturated saline, and was then dried over magnesium sulfate. After the solvent had been distilled away, the residue was purified by silica gel column chromatography using, as an eluent, hexane:ethyl acetate=9:1, to obtain 125 mg of a product of interest (yield: 13%).

Scheme 2

[Formula 8]

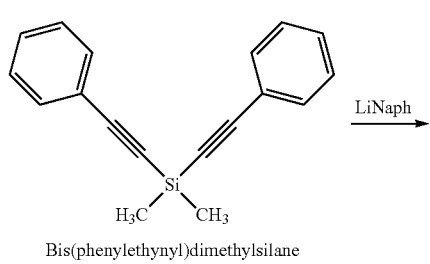

Bis(phenylethynyl)dimethylsilane

-continued

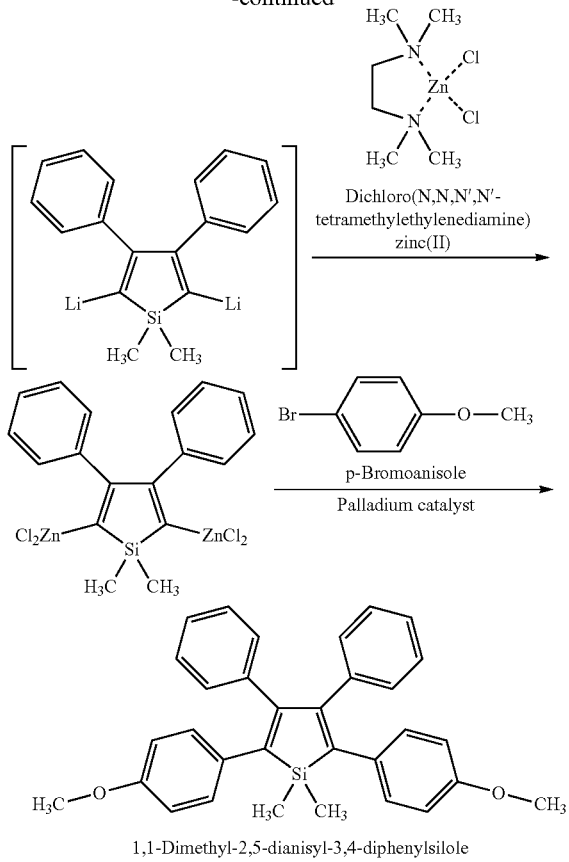

1,1-Dimethyl-2,5-dianisyl-3,4-diphenylsilole

4. Synthesis of Fine Polystyrene Particles Containing 1,1,2,3,4,5-hexaphenylsilole (Crosslinkers: Divinylbenzene and 1,1-diallyl-2,3,4,5-tetraphenylsilole)

HPS (17.2 mg, 0.032 mmol), 1,1-diallyl-2,3,4,5-tetraphenylsilole (DATPS) (33.6 mg, 0.072 mmol), and benzoyl peroxide having a purity of 75% (10.2 mg, 0.032 mmol) were dissolved in a mixed solution of styrene (251 mg, 2.41 mmol) and divinylbenzene (110 mg, 0.85 mmol).

Specifically, the inside of a two-necked eggplant flask equipped with an argon balloon, an Allihn condenser, a three-way cock and a septum was replaced with argon, and thereafter, 20 mL of a polyvinyl alcohol aqueous solution that had been prepared to a concentration of 1 g/L was added into the flask. While stirring the aqueous solution, the previously prepared monomer was added dropwise thereto (FIG. 7). After the reaction mixture had been fully dispersed, the inside of the synthetic system was kept at 80° C., and a polymerization reaction was carried out for 3 hours. After completion of the reaction, the solvent was removed by decantation, and the residue was then subjected to a heat treatment with distilled water at 80° C. and then, to washing with methanol. The obtained fine particles were dried under reduced pressure to obtain 79.9 mg of a product of interest (yield: 20%) (FIG. 8).

Besides, DATPS was produced with reference to Patent Literature 3, J. Organomet. Chem., 1990, 391:27, and the like.

5. Synthesis of Fine Polystyrene Particles Containing 1,1,2,3,4,5-hexaphenylsilole, Each Having Surface Modified with Hydroxy Groups (Crosslinker: Divinylbenzene)

HPS (71.5 mg, 0.13 mmol) and benzoyl peroxide having a purity of 75% (42.0 mg, 0.13 mmol) were dissolved in a mixed solution of styrene (1.0 g, 9.60 mmol) and divinylbenzene (477 mg, 3.67 mmol).

Specifically, the inside of a two-necked eggplant flask equipped with an argon balloon, an Allihn condenser, a three-way cock and a septum was replaced with argon, and thereafter, 20 mL of a polyvinyl alcohol aqueous solution that had been prepared to a concentration of 1 wt % was added into the flask. While stirring the aqueous solution, the previously prepared monomer was added dropwise thereto (FIG. 3). After the reaction mixture had been fully dispersed, the inside of the synthetic system was kept at 80° C., and a polymerization reaction was carried out for 3 hours. After completion of the reaction, the solvent was removed by decantation, and the residue was then subjected to a heat treatment with distilled water at 80° C. and then, to washing with methanol. The obtained fine particles were dried under reduced pressure.

After completion of the drying, an argon balloon, an Allihn condenser, a three-way cock, and a septum were equipped into this two-necked eggplant flask again, and the inside of the flask was replaced with argon. Then, 20 mL of Milli-Q was placed into the flask. While stirring, a mixed solution of 4-acetoxystyrene (AS) (500 mg, 3.08 mmol) and divinylbenzene (25.0 mg, 0.19 mmol), in which benzoyl peroxide (10.0 mg, 0.031 mmol) was dissolved, was added dropwise thereto, followed by swelling for 30 minutes. After completion of the swelling, the inside of the synthetic system was kept at 70° C., and a polymerization reaction was carried out for 4 hours. At this stage, IR spectrum was measured. As a result, a peak characteristic for carbonyl groups could be confirmed.

Twenty hours after completion of the reaction, 20 mL of a 1 M sodium hydroxide aqueous solution was added to the reaction mixture, and a hydrolysis reaction was then carried out for 4 hours. After completion of the reaction, the solvent was removed by decantation, and the residue was washed with methanol and was then dried under reduced pressure to obtain 1.16 g of fine particles of interest (yield: 59%) (Scheme 3) (FIG. 9). At this stage, IR spectrum was measured. As a result, a peak derived from carbonyl groups was reduced, and a broad peak derived from hydroxy groups could be confirmed (FIG. 10).

Scheme 3

[Formula 9]

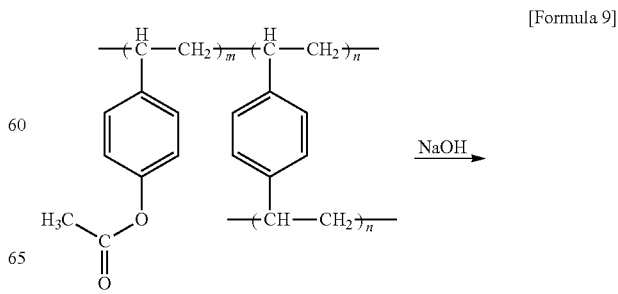

-continued

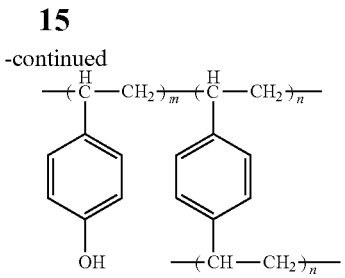

6. Comparison in Terms of Luminance and Fluorescence Quantum Yield Among Addition of Highly Planar Fluorescent Compound with Extended π-Conjugated System (Coumarin 6) and Addition of AIE-Active Compounds (TPS and APS) to Polystyrene Network Polymer Coumarin 6 (Tokyo Chemical Industry Co., Ltd.), TPS and APS were each incorporated into a polystyrene network polymer in the same manner as the methods for producing fine fluorescent particles described in 1 and 3 above, and the luminance and fluorescence quantum yield of individual fine fluorescent particles were then measured (FIG. 11).

The amount of coumarin 6 incorporated was set at 0.01, 0.05, 0.1, 0.15, 0.2 and 0.3 mol %. When a larger amount of coumarin 6 intended to be incorporated, it became difficult to form fine particles. In contrast, the amount of silole incorporated could be 0.1, 1.0, and 2.0 mol %. In addition, according to visual observation, fine particles, into which AIE-active siloles (TPS, APS and HPS) had been incorporated, emitted apparently strong light. The results obtained by measuring the luminance and fluorescence quantum yield of individual fine particles are shown in FIG. 11.

The luminance of fine polystyrene particles, into which coumarin 6 had been incorporated, was increased depending on the amount of coumarin 6, but it was much lower than the luminance of fine polystyrene particles containing an AIE-active compound at the same incorporation percentage as that of the fine polystyrene particles containing coumarin (FIG. 11, luminance).

In addition, the fluorescence quantum yield of the fine polystyrene particles, into which coumarin 6 had been incorporated, was increased depending on the amount of coumarin 6, until the incorporation percentage became approximately 0.2 mol %. However, at the incorporation percentage higher than 0.2 mol %, the fluorescence quantum yield of the fine polystyrene particles was decreased. These results suggest that an increase in the amount of coumarin 6 incorporated caused the concentration quenching of fluorescence. On the other hand, the fluorescence quantum yield of fine polystyrene particles, into which an AIE-active compound, TPS, APS or HPS, had been incorporated, was increased, as the incorporated amount was increased. When the incorporation percentage of TPS and APS was 2.0 mol %, the fluorescence quantum yields thereof reached 70% and 90%, respectively. This is considered because siloles are aggregated in the resin or are enclosed in the polystyrene resin, so that AIE effects are exhibited due to inhibition of the molecular movement of the siloles.

Moreover, FIG. 12 shows fluorescence micrographs of fine polystyrene particles containing 1,1,2,3,4,5-hexaphenylsilole (a1 and a2), and fluorescence micrographs of fine polystyrene particles containing coumarin 6 (b1 and b2). When the two types of fine polystyrene particles are compared with each other, it is found that the luminance of the fine polystyrene particles containing 1,1,2,3,4,5-hexaphenylsilole is higher than the luminance of the fine polystyrene particles containing coumarin 6. In particular, when the micrographs with a long exposure time are compared with each other (a1 and b1), the difference is clearly seen.

From the aforementioned results, it was found that when an AIE-active compound is used as a fluorescent substance in the production of fine fluorescent resin particles, the fluorescent substance enclosed in the resin exhibits AIE effects and thus, the resin emits light with higher efficiency than a common π-conjugated system fluorescent substance.

INDUSTRIAL APPLICABILITY

The fine fluorescent particle according to the present invention is excellent in terms of both luminance and fluorescence yield percentage, in comparison to the existing fine fluorescent particles. Therefore, by using the present fine fluorescent particle as a labeling substance, a target substance of interest can be clearly detected, and thus, it is anticipated that the present fine fluorescent particle will be used in diagnosis and the like in the medical field.

The invention claimed is:

1. A fine fluorescent particle containing an AIE-active compound, wherein the particle consists of a network polymer.

2. The fine fluorescent particle according to claim 1, which is characterized in that the ATE-active compound is a compound represented by the following formula (1):

[Formula 1]

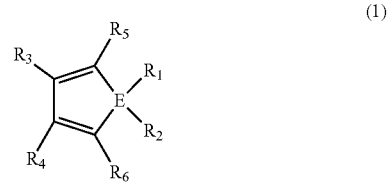

wherein E represents silicon or germanium; $R_1$ and $R_2$, which are the same or different, each represent a hydrocarbon group containing 1 to 6 carbon atoms, or a substituted or unsubstituted phenyl group; and $R_3$, $R_4$, $R_5$ and $R_6$, which are the same or different, each represent a substituted or unsubstituted phenyl group.

3. The fine fluorescent particle according to claim 1, which is characterized in that the $R_1$ and/or $R_2$ represent a phenyl group or a hydrocarbon group containing 1 to 6 carbon atoms.

4. The fine fluorescent particle according to claim 1, which is characterized in that the $R_3$, $R_4$, $R_5$ and/or $R_6$ represent any one of p-$((CH_3)_2N)C_6H_4$, p-$CH_3OC_6H_4$, p-$CH_3C_6H_4$, $C_6H_5$, p-$F_3CC_6H_4$, p-$(NO_2)C_6H_4$, m-$CH_3C_6H_4$, m-$FC_6H_4$, m-$F_3CC_6H_4$, 1-naphthyl, 2-styryl, biphenyl, 2-thienyl, bithienyl, 5-(2-benzo[b]thienyl)2-thienyl, 2-thiazole, 2-pyridyl, 3-pyridyl, N-methyl-2-pyrrolyl, 2,4,6-trimethylphenyl (Mes), or 2,4,6-triisopropylphenyl (Tip).

5. The fine fluorescent particle according to claim 1, which is characterized in that the network polymer is a vinyl polymer that is crosslinked by a diene.

6. The fine fluorescent particle according to claim 5, which is characterized in that the vinyl polymer is synthesized using, as a monomer(s), one or more selected from the group consisting of substituted or unsubstituted styrene, vinyl acetate, vinyl chloride, acrylonitrile, methacrylonitrile, vinylidene cyanide, propylene, isobutene, N-vinylcarbazole, methyl vinyl ketone, vinylpyridine, nitroethylene, acrylic acid ester, methacrylic acid ester, cyanoacrylic acid ester, vinyl ether, and an AIE-active compound having an alkenyl group.

7. The fine fluorescent particle according to claim 5, which is characterized in that the diene is any one selected from the group consisting of isoprene, butadiene, and divinylbenzene.

8. The fine fluorescent particle according to claim 5, which is characterized in that the network polymer is a polymer represented by the following formula (3) that is crosslinked by a diene:

[Formula 2]

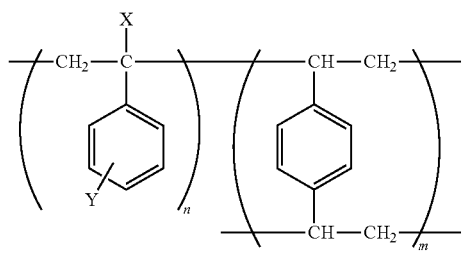

(3)

wherein X represents hydrogen or a hydrocarbon group containing 1 to 6 carbon atoms; Y represents hydrogen, an alkoxy group containing 1 to 6 carbon atoms, an alkyl group containing 1 to 6 carbon atoms, an acyl group containing 1 to 6 carbon atoms, or a carboxylate group containing 1 to 6 carbon atoms; and n and m each represent an integer, and n:m=1:0.2 to 2.

9. The fine fluorescent particle according to claim 6, which is characterized in that the AIE-active compound having a vinyl group is a compound represented by the following formula (2):

[Formula 3]

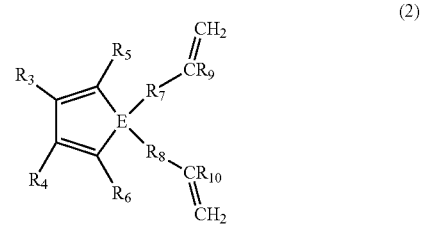

(2)

wherein E represents silicon or germanium; $R_3$, $R_4$, $R_5$ and $R_6$, which are the same or different, each represent a substituted or unsubstituted phenyl group; $R_7$ and $R_8$, which are the same or different, each represent a hydrocarbon chain containing 1 to 6 carbon atoms, or an aryl group; and $R_9$ and $R_{10}$, which are the same or different, each represent hydrogen or an alkyl group containing 1 to 6 carbon atoms.

10. The fine fluorescent particle according to claim 9, which is characterized in that the network polymer is a polymer represented by the following formula (4) that is crosslinked by a diene:

[Formula 4]

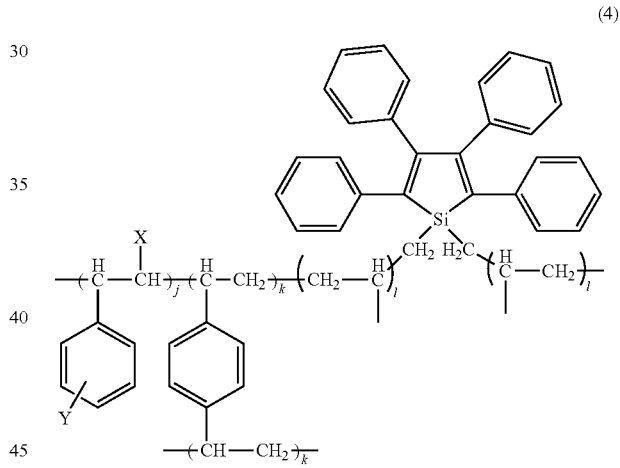

(4)

wherein X represents hydrogen or an alkyl group containing 1 to 6 carbon atoms; Y represents hydrogen, an alkoxy group containing 1 to 6 carbon atoms, an alkyl group containing 1 to 6 carbon atoms, an acyl group containing 1 to 6 carbon atoms, or a carboxylate group containing 1 to 6 carbon atoms; and j, k and l each represent an integer, and j:k:l=1:0.2 to 2:0.01 to 0.1.

* * * * *